United States Patent [19]

Sarosiek et al.

[11] Patent Number: 5,314,409
[45] Date of Patent: May 24, 1994

[54] CATHETER FOR ESOPHAGEAL PERFUSION

[75] Inventors: Jerzy Sarosiek; Richard W. McCallum; Ravinder K. Mittal, all of Charlottesville, Va.

[73] Assignee: UVA Patents Foundation, Charlottesville, Va.

[21] Appl. No.: 29,440

[22] Filed: Mar. 11, 1993

[51] Int. Cl.$^5$ .............................................. A61M 25/00
[52] U.S. Cl. ......................................... 604/101; 604/45
[58] Field of Search ................... 604/280, 101, 43, 45, 604/96; 128/658

[56] References Cited

U.S. PATENT DOCUMENTS

| | | | |
|---|---|---|---|
| 2,854,982 | 10/1958 | Pagano | 604/101 |
| 3,394,705 | 7/1968 | Abramson | 604/43 |
| 4,100,246 | 7/1978 | Frisch | 604/101 |
| 4,423,725 | 1/1984 | Baran et al. | 604/43 |
| 4,676,778 | 6/1986 | Nelson, Jr. | 604/45 |
| 4,714,460 | 12/1987 | Calderun | 604/43 |
| 5,071,406 | 12/1991 | Jang | 604/101 |

Primary Examiner—Paul J. Hirsch
Attorney, Agent, or Firm—Sheldon H. Parker

[57] ABSTRACT

An esophageal perfusion catheter, having an outer housing, a plurality of flexible, tubular channel members within said outer housing, and at least two spaced balloon members encompassing said catheter. Two of the channel members are in fluid communication with each of two balloons. One of the balloons is about 150 millimeters from the distal end of said catheter and about 75 millimeters from the other balloon. A third of the tubular channel members is an esophageal perfusion aspirating channel and is in communication with a port at the distal end of the catheter. A fourth of the tubular channel members serves as a gastric aspirating channel. A fifth of the tubular channel members serves as an aspirating channel. The sixth channel member, serves as an air vent. The esophageal perfusion aspirating channel has a ID of about 3 millimeters. The gastric aspirating channel has a ID of about 2 millimeters. The two channel members which communicate with the balloons have a ID of about 1 millimeter. The interior space between the outer housing and the channel members can be filled with silicone.

11 Claims, 3 Drawing Sheets 5,314,409

CATHETER FOR ESOPHAGEAL PERFUSION

BACKGROUND OF THE INVENTION

1. Field of the Invention

Catheter for esophageal perfusion and for the study of human esophageal secretion.

2. Brief Description of the Prior Art

An insight into the pathogenesis of esophageal diseases, such as reflux esophagitis, esophageal ulcer, Barrett's esophagus, esophageal stricture or esophageal cancer has been hampered by a lack of methodology for the study of esophageal secretory function of esophageal mucosa in health and disease. Therefore knowledge in the area of the esophageal mucosal protective mechanisms, especially in humans has been highly hypothetical.

SUMMARY OF THE INVENTION

The esophageal perfusion catheter of the instant invention includes, an outer housing, a plurality of flexible, tubular channel members within said outer housing and at least two spaced balloon members encompassing said catheter. One of the tubular channel members is in fluid communication with a one of the balloons, and another of the tubular channel members is in fluid communication with the other of the balloons.

A third of tubular channel member serves as an esophageal perfusion aspirating channel and is in fluid communication with at least one port at the distal end of the catheter. A fourth tubular channel member serves as a gastric aspirating channel and is in fluid communication with a plurality of ports positioned at the distal end of the catheter. At the opposite end of the catheter, each channel member is connected to a stop cock, which provides valving between the channel members and the aspirating devices, source of perfusate, collection member for gastric fluid and the like.

A fifth tubular channel member is an aspirating channel, and is in communication with a port above the second balloon. A sixth channel member is an air vent and is in fluid communication with a port positioned just below the upper balloon.

While the exact ID of the channels is not narrowly critical, the size of the esophageal perfusion channel is preferably about 3 millimeters. The esophageal perfusion channel is in fluid communication with two ports proximate to, and above, the first balloon. The gastric aspirating channel has a preferred ID of about 2 millimeters and the balloon inflating channel members have a preferred ID of about 1 millimeter. The gastric aspirating channel and the aspirating channel above the upper balloon have preferred ID's of about 2 millimeters. Preferably, the balloons are spaced apart on the order of about 75 millimeters and the lower balloon is spaced on the order of about 150 millimeters from the distal end of the catheter.

The interior space between the outer housing and the channel members is filled with a flexible polymeric material, preferably silicone.

DESCRIPTION OF THE PREFERRED EMBODIMENTS

The catheter of the instant invention is a multichannel catheter equipped with at least two balloons. The balloons which are provided makes the study of the esophageal mucosal secretion technically feasible and adequate. Through modifications, the catheter can be used in the study of the esophageal secretory function both in experimental animals and humans. The catheter design also provides the ability to explore the secretory response of the esophageal mucosa to physiological concentrations of damaging factors such as acid, pepsin, bile acids, etc. playing the major role in the development of esophageal diseases.

Figure 1:
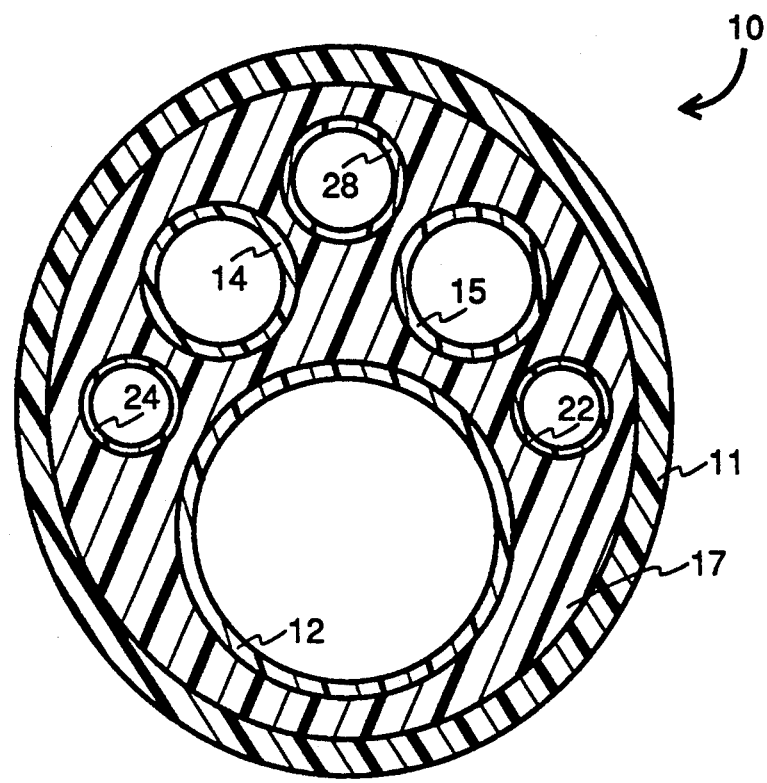
FIG. 1 is a schematic cross-sectional view of catheter of the instant invention.
Figure 2:
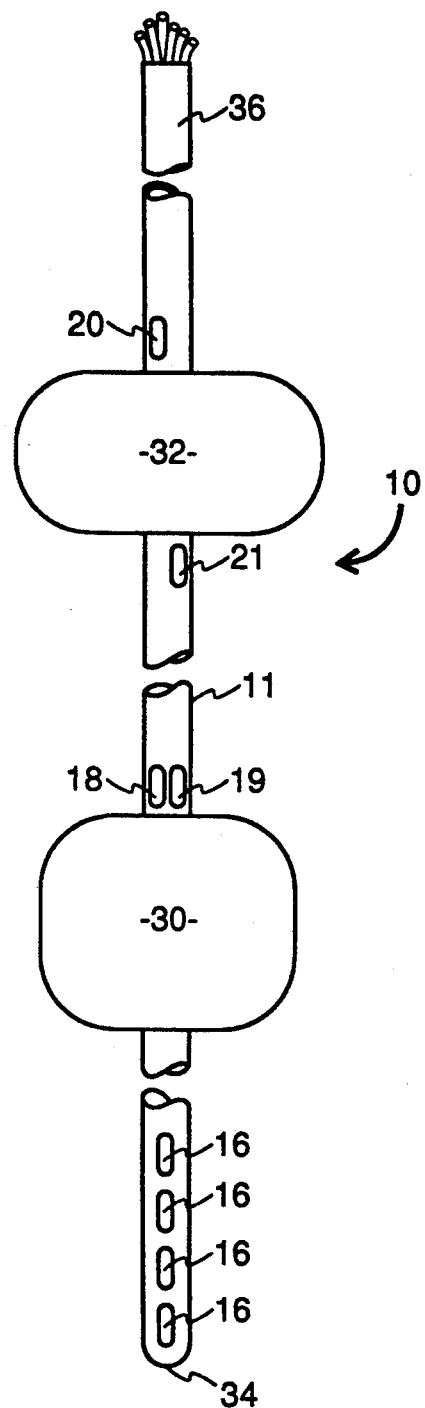
FIG. 2, is a longitudinal view of the catheter of FIG. 1.

The catheter, indicated generally as 10, in FIGS. 1 and 2, is comprised of 6 channels as illustrated in FIG. 1. The largest channel 12 has a 3 mm ID, and serves as a major aspiration channel of the mucosal secretion. Channel 12 can be used both as influx and efflux channel. Another channel 28, serves as the air vent and is has a 1 mm ID. It can also serves as an influx channel for esophageal perfusion or air vent channel if the major 3 mm channel is used both for an influx and an efflux of perfusate. Sideports 16, for these channels are spaced adequately to secure a total recovery of esophageal perfusate or secretion in semirecumbent position of the patient during the procedure. The aspirating channel 14, for aspirating above the upper balloon 32 can have a 2 mm ID. The gastric aspirating channel 15, has an ID of 2 mm and is in fluid communication with the four ports 16, at the tip 34, of the catheter 10.

The other two channels, 22 and 24, are 1 mm ID each, and serve for inflation of upper and the lower balloon, respectively, to the size securing the adequate sealing of 7.5 cm esophageal segment, chosen for the esophageal secretory study. These channels have ports opening to their respective balloons 30 and 32, and otherwise are dead ended. The balloons encompass, encircle, engird the catheter. They each have a length of about 20 mm and are inflatable as required. The balloon are formed from an inflatable material such as latex.

The placement of esophageal catheter in reference to the lower esophageal sphincter can be monitored owing to the catheter scale marked in centimeters. This catheter can serve for the study of the upper, or the lower 7.5 cm segment of esophagus. For the study of the entire esophagus, both balloons can be spaced about 19-20 cm apart. The catheter also lends itself to further modifications, as for example, for the separate study of esophageal secretion of the upper and the lower esophagus by adding one more balloon located above the upper balloon. The distance from the lower end, or distal end of the catheter to the lower balloon can be on the order of about 150 mm, the distance between the upper and lower balloons about 75 mm and the total length of the catheter from the distal end to the upper end, about 1120 mm. Scale marks are provide every 10 cm, starting from the lower end of the lower balloon, with the region between 35 and 45 cm, marked every centimeter.

The next channel 15, with a 1.5 mm ID serves for aspiration of the gastric secretion both before the study and after the esophageal secretion study. Measuring the content of esophageal perfusion marker leaking into the gastric compartment from the sealed esophageal segment will serve for the study of the recovery rate of esophageal perfusate. The last channel 14, is provided with a 1.5 mm ID and serves for the study of esophageal and/or salivary secretion accumulating above the upper balloon.

In summary, the balloon channels 22 and 24 communicate with the balloons 32 and 30, through ports not illustrated. Channel 12 communicates with ports 18 and 19. The aspirating channel 14 communicates with port 20 above the upper balloon. Air vent channel 28 communicates with port 21 just below the upper balloon 32. Gastric aspirating channel 15 communicates with the plurality of ports 16, located at the tip or distal end 34 of the catheter.

The tubes 12, 14, 15, 22, 24, and 28 extend from the upper end 36 of the outer catheter tube 11 and are connected to two or three way stop cocks. The stop cocks are in turn, in communication with aspiration equipment, source of perfusate and the like.

The space between the six tubes which form the channels and the catheter 11, is filled with a silicone polymer 17, or other essentially inert, flexible material. The silicone serve to provide the requisite level of rigidity to the catheter. The typical materials for construction of the catheter are well known in the prior at art. For example, elastomeric materials such as urethane have been used particularly where soft flexible material is required. Tubing materials include an extrudable polyvinyl chloride, medium density polyethylene, polypropylene, high density polyetheylenpolycarbonates and nylon.

Figure 3:
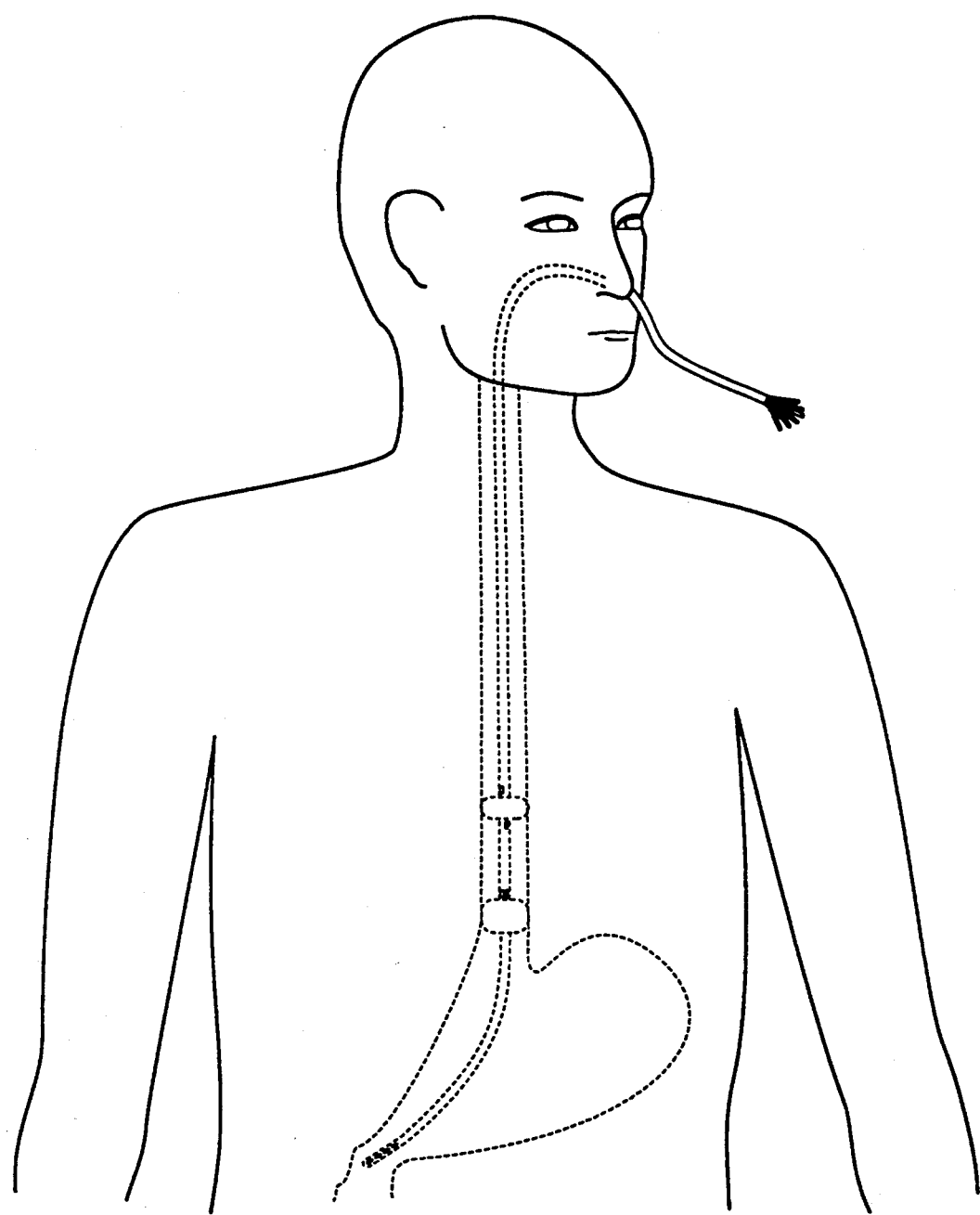
FIG. 3, is a schematic illustration of the catheter as it is used in a human.

The clinical use of esophageal perfusion catheter is schematically illustrated in FIG. 3.

EXPERIMENTAL USE OF THE CATHETER

A new experimental model of esophagitis in the cat: The role of esophageal mucus and bicarbonate in mucosal protection against peptic erosion and back-diffusion of hydrogen ion.

While the focus moves from the stomach to the esophagus, the interrelationship between aggressive factors, mainly of gastroduodenal origin, and various protective components that are elaborated within the esophageal mucosa or in the salivary secretion, is discussed.

Aggressive factors can be assembled into three major categories:
I. Gastroduodenal in origin:
1) Originating in the gastric compartment:
   A. Hydrochloric acid.
   B. Proteolytic activity of pepsins.
   C. Potentially damaging but still not adequately explored lysolecithin.
   D. Eventually the leukotriens.
2) Duodenal in origin:
   A. Trypsin.
   B. Bile acids.
   C. Still hypothetically phospholipase $A_2$.
II. Exogenous iatrogenic agents:
   A. Radiation.
   B. Mainly topical irritants, such as: a/NSAIDs, b/steroids, c/quinidine, d/emepronium bromide, e/potassium chloride, f/tetracyclines (etc.).
III. Exogenous non-iatrogenic agents:
   A. Corrosives.
   B. Alcohol.
   C. Infections.

The protective factors combating these aggressive agents can also be divided into three broad categories:
I. Salivary in origin:
1. Confirmed in clinical studies:
   A. Bicarbonate.
   B. Total buffering capacity,
   C. Epidermal growth factor.
2. Hypothetical:
   A. Mucus and mucin.
   B. Phospholipids.
   C. Prostaglandins.
   D. Prostacyclines.
II. Originating within the esophageal mucosa:
1. Well established in an experimental setting only:
   A. Bicarbonate.
   B. Hydrophobic lining of the esophageal mucosa.
   C. Intercellular tight junctions.
   D. Intercellular sialomucin and lipids.
   E. $Na^+/H^+$ antiport.
   F. Proliferative activity of the striatum germinativum.
   G. Mucosal blood flow.
2. Hypothetical:
   A. Mucus and mucin.
   B. Phospholipids.
   C. Prostaglandins.
   D. Prostacyclines.
   E. Leukotriens.
   F. Excitatory and inhibitory esophago-salivary reflexes.
III. Extramucosal:
1. Well established in experimental and clinical studies:
   A. Adequate basal lower esophageal sphincter pressure.
   B. Competence of the lower esophageal sphincter.
   C. Adequate amplitude, duration and frequency of primary peristalsis.
   D. Well established secondary peristaltic waves.
   E. Effective gastric emptying.

There have been numerous studies and many reports on the mechanism of damage to the esophageal mucosa by aggressive agents, but the nature of mucosal protective factors operating at the surface epithelium still remains undetermined. Although the main mechanism and sequence of events leading to gastroesophageal reflux can vary in individual settings, hydrochloric acid and the proteolytically active pepsin are the ultimate aggressive factors damaging the esophageal mucosa.

The damaging role of acid and pepsin in reflux esophagitis has been clearly established but we do not fully understand some of the underlying pathomechanisms. Therefore, as a background to mucosal defense against acid and pepsin is bicarbonate, potentially embedded into the unstirred layer of mucus and facilitating a maintenance of a pH gradient across the mucusbicarbonate complex.

In the past in vivo studies of esophageal mucosa have been limited by an inability to accurately separate the loss of hydrogen ions from the esophageal perfusate due to a back diffusion, from hydrogen ions lost as a result of intraluminal neutralization through the normal secretion of bicarbonate. This phenomenon always compromised the results or such studies. Some of these shortcomings, are addressed in the new model of esophageal perfusion, by using tritium-[$^3$H]. In the new experimental model it is possible to assess the role of a mucusbicarbonate complex in mucosal protection. As a marker of the damage to esophageal mucosa the concentration of hemoglobin in the esophageal perfusate is utilized.

To this point we have studied five cats. Esophageal perfusion was performed with a specially designed tube with two balloons. One balloon sealed the esophagus proximally just below the upper esophageal sphincter, the other one was located above the lower esophageal sphincter.

Four ports were present, one for each balloon, one for the perfusate and one for confirmation that tritium did not leak into the gastric compartment. The 2 balloons are approximately 11 cm apart.

Using this perfusion device, we were able to modify the perfusate solution. NaCl was used during four 10 min. periods, hydrochloric acid alone or with pepsin during the next four 10 min. periods and again NaCl during the last eight 10 min. experimental periods. In each 10 min. period a fresh perfusate was introduced into the esophageal compartment.

Three different esophagitis models were developed. In a severe chronic esophagitis scenario esophageal ulcers and even strictures develop and this takes approximately two perfusions (with HCl and pepsin) per week for a month. A non-complicated yet chronically inflamed esophagus results from perfusion once a week over a four week period. A self-limiting damage results from one perfusion with recovery over a two week period.

The esophagus was perfused with 0.9% NaCl in a control experiment during 16 consecutive 10 min. periods. In experiments leading to the development or esophagitis the esophageal mucosa was perfused with 0.9% NaCl during first four 10 minutes periods and then 0.5 mg/ml HCl with 0.5 mg/ml of pepsin was substituted for sodium chloride. After four consecutive 10 min. periods of perfusion with HCl-pepsin solution, a perfusion with sodium chloride was reinstalled for the next consecutive eight 10 min. periods. All solutions were equilibrated with tritiated water $[^3H]_2O$. At the end of each 10 min. period perfusate was recovered and a fresh solution introduced into esophageal compartment.

Back-diffusion of hydrogen ion was measured using a beta scintillation counter. Secretion of esophageal mucus glycoprotein (mucin) was measured by Alcian blue uptake methodology according to Hall et al. (3). as we described previously (4), slightly modified to esophageal perfusate conditions. An Alcian blue uptake was measured at pH 5.8 (for fucomucin), pH 2.5 (for predominantly sialomucin) and at pH 1.0 (for predominantly sulphomucin). The sum of all three mucins was expressed as total mucin. Secretion of bicarbonate was measured by a back-titration method (5,6). The leakage of serum elements was estimated by the measurement of the content of hemoglobin in recovered perfusate by calorimetric method (Sigma Dgn. Kit#527).

Results are presented as a mean value ISD of first four 10 min. periods (1-st 40 min), representing always perfusion with sodium chloride, second four consecutive 10 min. periods (2-nd 40 min) referred to perfusion with NaCl in control study or HCl-pepsin in esophagitis experimental scenario, third and fourth consecutive four 10 min. periods (3-rd and 4-th 40 min) representing perfusion with sodium chloride.

The esophagus in these cats was evaluated by performing endoscopy before each perfusion session in order to assess the base-line conditions. Statistical analysis was evaluated by Student's paired "t" test performed with the "StatSoft" software package.

RESULTS

After long-term perfusion (two perfusions a week for four weeks) animals developed a severe esophagitis with esophageal ulcers located in a lower one/third of esophagus with subsequent stricturing such that a 3 mm diameter remaining would not allow passage of a pediatric endoscope.

The appearance of the esophageal mucosa in an acute perfusion model where perfusion took place for sixteen 10 min. periods and then the animal was sacrificed 40 min. later, is more like the human esophagitis changes with erosions present. This is in contrast the severe stricturing and ulceration previously described.

An exposure of esophageal mucosa to sodium chloride, during 160 min., equilibrated with tritium $[^3H]$, led to a slow, but steady loss of the hydrogen ion (radioactivity) from the lumen at the rate of 15 pEq/cm$^2$/10 min. Thus, esophageal mucosa does not seem to be a leaky barrier at near neutral pH. 40 minutes of exposure of the same mucosa to 0.15 m HCl with 0.5 mg/ml of pepsin leads to an obvious diffusion of hydrogen ion with a progressive loss of radioactivity of luminal tritium. Actually, the highest rate of the net loss of hydrogen ion from the luminal solution was 19 microEq/10 min./cm$^2$ and was statistically significant (p<0.005). An increase in the permeability of esophageal mucosa was sustained despite withdrawal or HCl/pepsin solution and its substitution with sodium chloride during the next two 40 min. periods. There was, however, a trend towards the gradual resurrection or permselectivity of the esophageal barrier lost during the acid-pepsin perfusion. At the end of an experimental procedure, the permeability barrier was restored in over 91%.

The esophageal mucosal response in terms of bicarbonate secretion was enormous immediately upon beginning the acid-pepsin perfusion. The relative bicarbonate secretion increased from 0.5 basally to almost 350 nEq/10 min./cm$^2$ (p<0.001) when acid-pepsin solution was introduced into esophageal perfusate. The increase in bicarbonate secretion was parallel, in terms of experimental procedure time, to an increase in the rate of hydrogen ion back-diffusion, occurring in the second 40 min period.

The basal rate of bicarbonate secretion in cat esophageal mucosa was approximately 0.5 nEq/cm2/10 min.. The basal rate of hydrogen ion back diffusion was 0.015 nEq/cm2/10 min.. Thus the rate of bicarbonate secretion was 33 times higher than the value of hydrogen ions penetrating the mucosa. The rate of hydrogen ion diffusion into esophageal mucosa during the first 10 min. period of HCl/pepsin perfusion (pH 0.95) reached 1 microEq/cm$^2$/10 min.. Thus basal secretion of bicarbonate in the esophageal mucosa is inadequate to combat this hydrogen ion diffusing into the esophageal mucosa. In this first 10 min. period of the exposure to the HCl/pepsin solution, however, we immediately observed an approximately 1000-fold increase of esophageal bicarbonate secretion, over the basal rate of bicarbonate generation. This increase, however, was still 50% lower than that which would be required to completely neutralize hydrogen ion. During the next three 10 min. periods the ratio between the rate of bicarbonate secretion and the rate of diffusion of hydrogen ion into the mucosa underwent further deterioration and reached the value 0.02 at the end or 40 min perfusion with HCl-pepsin. This is probably why we observed a progressive damage to the esophageal mucosa resulting in an enormous increase of the content of hemoglobin in our perfusate.

In normal conditions, when sodium chloride was the only constituent of the bathing solution, we observed only trace amounts of hemoglobin in esophageal perfusate. During perfusion with HCl-pepsin, however, the content of hemoglobin dramatically increased ($p<0.001$). This increase showed a surprisingly fast trend towards normalization, when the acidic perfusate was replaced with saline. Thus, we believe, that an increase in the content of hemoglobin is indicative of a loss of mucosal integrity and that an increase in bicarbonate secretion at the end of HCl-pepsin perfusion was also partly due to the leakage from the serum.

Secretion of esophageal mucus, estimated on a basis of the sum of fucomucin (measured at pH 5.8), sialomucin (measured at pH 2.5), and sulphomucin (at pH 1.0) with Alcian blue uptake methodology in control experiment (saline perfusate) was the highest during the first 40 min. period and reached plateau during the next three consecutive 40 min periods. HCl-pepsin solution, introduced into the esophageal compartment after the first 40 min period, evoked a sustained release of esophageal mucus into the perfusing solution. There was a 2.5 fold increase over the control study in the second 40 min period ($p<0.01$) and a 2 fold increase during the third 40 min. period ($p<0.02$).

This increase of the content of esophageal mucus in the bathing solution could be due to an increase of the content of the newly secreted mucus from the mucosal glands and partly due to a proteolytic cleavage of esophageal mucus layer by perfusing pepsin. To confirm this hypothesis we plan to further analyze the macromolecular structure of our recovered mucus from the perfusate. Both mechanisms of mucus release into the bathing solution presumably lead to a decrease of the content of mucosal mucus thus attenuating the esophageal mucosal barrier. In such a way compromised esophageal mucosa might be more susceptible to the damage by hydrogen ion.

The model of experimental esophagitis as a very promising and reliable tool not only for the future study of the pathomechanism of inflammation but also for the investigation of the development of complications such as esophageal ulcer and/or strictures.

Although cat esophageal mucosa represents a tight type of epithelium at neutral pH, at pH 0.95, however, it becomes significantly leaky. The mechanisms of this transfer from the tight to the leaky state under the influence of HCl/pepsin solution remains unknown.

An enormous release of esophageal mucus and bicarbonate during the challenge of esophageal mucosa with HCl and pepsin may indicate their crucial role in esophageal protection.

The measurement of hemoglobin in esophageal perfusate seems to be a good indicator of a serum leakage resulting from the damage of the esophageal mucosa.

The novel esophageal perfusion model, equilibrated with tritium [$^3$H] is a very convenient method for the simultaneous measurement of a back diffusion of hydrogen ion and secretion of esophageal bicarbonate and is adaptable for use in the human esophagus.

Esophageal perfusion, with a full recovery of esophageal perfusate, seems to represent a very promising approach to the study of biochemical changes reflecting damage by the perfusing compounds to the esophageal mucosa.

What is claimed is:

1. An esophageal perfusion catheter, the catheter comprising:
    an outer housing,
    a plurality of flexible, tubular channel members within said outer housing, at least two spaced balloon members encompassing said catheter,
        a first of said tubular channel members being in fluid communication with a first of said at least two balloons, said first balloon being closer to the distal end of said catheter than the second balloon,
        a second of said tubular channel members being in fluid communication with a second of said at least two balloons,
    a third of said tubular channel members being an esophageal perfusion aspirating channel and being in communication with at least one port, said at least one port being at the distal end of said catheter,
    a fourth of said tubular channel members being a gastric aspirating channel, said gastric aspirating channel being in fluid communication with a plurality of ports positioned at the distal end of the catheter,
    a fifth of said tubular channel members being an aspirating channel, said fifth channel member being in communication with a port above said second balloon, and
    a sixth channel member, said sixth channel member being an air vent and being in fluid communication with a port positioned below and proximate the second balloon.

2. The esophageal perfusion catheter of claim 1, wherein said esophageal perfusion channel has a ID of about 3 millimeters.

3. The esophageal perfusion catheter of claim 1, wherein said gastric aspirating channel has a ID of about 2 millimeters.

4. The esophageal perfusion catheter of claim 1, wherein said first and said second channel members have a ID of about 1 millimeter.

5. The esophageal perfusion catheter of claim 1, wherein said fifth channel has a ID of about 2 millimeters.

6. The esophageal perfusion catheter of claim 1, wherein the interior space between said outer housing and said channel members is filled with a flexible polymeric material.

7. The esophageal perfusion catheter of claim 1, wherein the interior space between said outer housing and said channel members is filled with silicone.

8. The esophageal perfusion catheter of claim 1, wherein said balloons are spaced apart on the order of about 75 millimeters.

9. The esophageal perfusion catheter of claim 1, wherein said first balloon is spaced on the order of about 150 millimeters from the distal end of said catheter.

10. The esophageal perfusion catheter of claim 1, wherein two ports are provided proximate to, and above, said first balloon, said ports being in communication with said third, esophageal perfusion aspirating channel.

11. The esophageal perfusion catheter of claim 10, further comprising a plurality of stop cocks, each channel member being connected to one of said stop cocks.

* * * * *